United States Patent [19]

Tournier

[11] Patent Number: 4,587,319

[45] Date of Patent: May 6, 1986

[54] SALIFIED ACRYLIC ALLYLOLIGOSACCHARIDE COPOLYMER, A PROCESS FOR PREPARING THE COPOLYMER, AND APPLICATION AS A SUPER-ABSORBENT

[75] Inventor: Herve Tournier, Valleiry, France

[73] Assignee: Beghin-Say S.A., Thumeries, France

[21] Appl. No.: 682,351

[22] PCT Filed: Mar. 16, 1984

[86] PCT No.: PCT/FR84/00066

§ 371 Date: Nov. 19, 1984

§ 102(e) Date: Nov. 19, 1984

[87] PCT Pub. No.: WO84/03706

PCT Pub. Date: Sep. 27, 1984

[30] Foreign Application Priority Data

Mar. 18, 1983 [FR] France ............................... 83 04488

[51] Int. Cl.$^4$ ............... A61L 15/00; C08F 216/12; C08F 220/04

[52] U.S. Cl. ........................... 527/313; 527/314; 526/238.2; 526/238.21; 526/238.22; 526/238.23; 604/367

[58] Field of Search ..................... 527/313, 314; 526/238.2, 238.21, 238.22, 238.23; 604/367

[56] References Cited

U.S. PATENT DOCUMENTS

| | | | |
|---|---|---|---|
| 2,606,881 | 8/1952 | Zief et al. | 526/309 |
| 2,719,970 | 10/1955 | Griffin et al. | 536/124 |
| 2,798,053 | 7/1957 | Brown | 424/57 |
| 4,076,663 | 2/1978 | Masuda et al. | 525/54.31 |
| 4,094,832 | 6/1978 | Söderberg | 536/51 |
| 4,094,833 | 6/1978 | Johansson et al. | 536/51 |

*Primary Examiner*—Ronald W. Griffin
*Attorney, Agent, or Firm*—A. W. Breiner

[57] ABSTRACT

The invention relates to liquid-absorbing products, in particular blood and urine. It concerns a salified acrylic allyloligosaccharide copolymer consisting in chemically combined form of at least one allyloligosaccharide with a mean degree of substitution of less than 4 per molecule and of at least one acrylic derivative with partly or totally salified carboxyl functions, said copolymer having a degree of retention, after 30 minutes in water salinated at 10 g/liter, exceeding 8 g of saline water per gram of copolymer.

Preferably the allyloligosaccharide is allylsaccharose with $\overline{DS}$ 2 and the acrylic derivative is acrylic acid.

The invention applies to using these polymers as additives to improve the absorption of absorbing materials used in personal hygiene.

21 Claims, No Drawings

SALIFIED ACRYLIC ALLYLOLIGOSACCHARIDE COPOLYMER, A PROCESS FOR PREPARING THE COPOLYMER, AND APPLICATION AS A SUPER-ABSORBENT

The invention concerns liquid-absorbing products, in particular blood and urine. Its object is a salified acrylic allyloligosaccharide copolymer and its application as a superabsorbent in personal hygiene, in agriculture, and as a moisture stabilizer. Another object is an allyloligosaccharide as an intermediate product. A further object is a process for preparing said acrylic allyloligosaccharide copolymer.

STATE OF THE ART

Two known documents of applicant already describe acrylic allyloligosaccharide copolymers. U.S. Pat. No. 2,606,881 describes the polymerization of allyldisaccharide such as allysaccharose with an acrylic derivative. Allyldisaccharide is prepared by etherifying all or part of the eight alcohol groups by an allyl group. Thus, a maximum of eight allyl functions can be borne by a disaccharide, namely a maximal degree of substitution (DS) of eight. U.S. Pat. No. 2,606,881 describes an allylsaccharose containing 6.5 allyl groups per molecule. The products obtained following copolymerization of the allyldisaccharide derivative with the acrylic derivative in a ratio by weight near unity, however, offer no significant absorbing property at all when immersed in saline water at 35° C. for 30 minutes in conformity with a standardized test described by Goldstein and Pierre (Marketing Technology Service, Sept. 16–18, 1981 - Absorbent Products Conference).

U.S. Pat. No. 2,798,053 discloses using acrylic allylsaccharose copolymers as ion-exchange resins. The allylsaccharoses offer a mean degree of substitution (number of allyl groups per saccharose molecule) exceeding 5 and are employed only at very low molar ratios. Moreover, they offer no absorbing property at all in the light of the above-cited test when they are copolymerized with an acrylic derivative. This document even states (Example 3) that if higher proportions of allylsaccharose are used, very hard polymers with little swelling are obtained. The invention goes against the disclosure of this document. The object of the invention on the contrary is to offer a new family of acrylic allyloligosaccharide copolymers with excellent absorbing properties.

DESCRIPTION OF THE INVENTION

In the invention, the salified acrylic allyloligosaccharide copolymer is characterized by consisting in a chemically combined form of at least one allyloligosaccharide with a mean degree of substitution less than 4 per molecule and of at least one acrylic derivative with partly or totally salified carboxyl functions, said copolymer having a degree of retention, following 30 minutes in g/liter of salt/water, exceeding 8 g of saline water per gram of copolymer.

As regards the oligosaccharides, the mean degree of substitution $\overline{DS}$ is defined as the number of allyl groups which have replaced hydroxyl groups in that molecule. It is obvious besides that during allyloligosaccharide synthesis, a mixture will be obtained and that the mean degree of substitution is computed on the basis of that mixture.

In this application the term oligosaccharide denotes sugars with one to ten glucide groups which are chemically bound according to the terminology of the Chemical Abstract. The glucide groups may correspond to chains containing five or six preferably cyclic carbon atoms such as glucose or fructose and their stereochemical isomers. These oligosaccharides, for example, are obtained by hydrolyzing such polymer substances as starch, glycogen, cellulose. Among the oligosaccharides suitable for the invention, the mono-, di-, tri-, and tetrasaccharides are preferred, and among these the disaccharides are preferred. Among such illustratively are saccharose (sucrose in English), maltose, cellobiose, lactose. Saccharose is preferred in this present invention.

The allyloligosaccharides are prepared in known manner, for instance by etherification, using an allyl halide of an alcohol function. The reaction formula is given by:

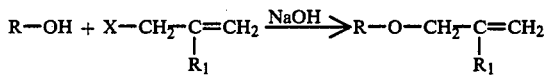

where
R = oligosaccharide radical
$R_1$ = H, $C_1$ to $C_4$ alkyl
X = Cl, Br

This process is illustrated with respect to saccharose allylation in U.S Pat. No. 2,719,970. This formula shows that the allyl derivative fixated on the oligosaccharide can be substituted on the $\beta$ carbon. Nevertheless, it is preferable within the scope of the invention to use the allyl derivative where $R_1$=H, that is the non-substituted allyl derivative. The above-cited documents only describe allyloligosaccharides of a high mean degree of substitution (>5.0) which cannot result in the copolymers of the invention. Therefore, another object of the invention are allyloligosaccharides with a mean degree of substitution less than 3.0 but higher than or equal to 1.0 as intermediate products to obtain acrylic allyloligosaccharide copolymers. This feature will be elaborated on in the final part of the description. The expression acrylic derivative covers all the derivatives with a double bond to a carboxyl group or a group capable of resulting in a carboxyl group by hydrolysis reaction (ester, nitrile, amide), said double bond not being substituted on the $\beta$ carbon, as indicated by the formula below:

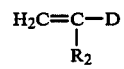

where
D = COOH, COOR$_3$, CONH$_2$, CN
$R_2$ = hydrogen atom or a $C_1$ to $C_4$ alkyl group
$R_3$ = a $C_1$ to $C_4$ alkyl group Among these illustratively are acrylic or methacrylic acid, branched or linear $C_1$ to $C_8$ saturated alkyl methacrylate, acrylate. However, acrylic or methacrylic acid shall be preferred. Again, those diacrylates obtained by esterifying a short carbon chain diol by acrylic acid can be considered, but they result in products of lesser performance. Again, it is possible to use acrylamide derivatives and preferably acrylamide or methacrylamide each alone or in mixture, also acrylonitrile. These acrylic derivatives in the copolymer are at least partly in salified form and preferably rendered such by an alkali cation such as potassium, sodium, or ammonium. Sodium and potassium are preferred within the scope of the invention. Preferably at least 10% of the carboxyl groups shall be salified. One of the physical properties allowing to characterize the copolymers of the invention is the absorbing capacity. Therefore, an absorption test has been devised with the following conditions:

The copolymer, placed in an inert pouch, is immersed at 35° C. for 30 minutes in a solution of NaCl at a proportion of 10 g/liter, then the product is centrifuged at 1200 g for one minute. The weight is measured before and after immersion, and the degree of retention is computed by comparison with a control. This degree of retention $R_{30}$ must exceed 8.

Preferably the mean degree of substitution per monomer group will be less than 3.0 and equal to or larger than 1.0. In order to obtain acrylic allyloligosaccharide copolymers with improved absorbing properties, these copolymers preferably shall consist of a mixture of allyloligosaccharides with a mean degree of substitution larger than or equal to 5 and of allyloligosaccharides with a mean degree of substitution per crosslinked group less than or equal to 3, the average of course being less than 4. This observation applies to the preferred copolymers $(1.5 \leq \overline{DS} \leq 3)$, that preferably the mixture shall consist of allyloligosaccharides with $\overline{DS} \leq 1.5$ and $\overline{DS} \geq 3$.

Now it was found in a surprising manner that this distribution improves the copolymer behavior with regard to absorbing capacity. As regards the respective proportions of allyloligosaccharides and acrylic derivatives constituting the copolymer, preferably it shall correspond to a molar allyl/acrylic ratio between 0.005 and 1, namely a ratio by weight in the case of the allylsaccharose couple with $\overline{DS}=2$/acrylic acid, a ratio of 0.03 to 6. In the case of the monoacrylicallyldisaccharides which are the preferred copolymers of the invention, the preferred limit proportions by weight can be defined as follows:

| allyldisaccharide | 5 to 30% |
| monoacrylic derivative | 70 to 95% |
| and preferably | |
| allyldisaccharide | 8 to 25% |
| monoacrylic derivative | 75 to 92% |

In the case of the allyldisaccharides with a low (near unity) degree of substitution, preferably there shall be a higher molar proportion on of allyldisaccharide, namely:

| allyldisaccharide | 15 to 30% |
| monoacrylic derivative | 85 to 70% |

Another object of the invention is the preparation of a salified allyloligosaccharide copolymer as described above which is characterized by reacting an acrylic derivative and an aqueous mixture of allyloligosaccharide with a mean degree of substitution less than 4 at a temperature in excess of 10° C. in the presence of a radical polymerization initiator in the presence of water, and by the obtained copolymer being partly or wholly salified by a strong mineral base, then being dried. In order to achieve better polymerization yields, preferably the water of the aqueous mixture shall be present in a proportion of 0.5 g per gram of allylsaccharose, even though it is possible that the reaction also can be carried out in the presence of very minute amounts of water (0.01 g/g) per gram of allylsaccharose.

Obviously every description above relating to the allyloligosaccharides and the acrylic derivatives applies equally to this part of the invention. Temperature also is a critical parameter and even though the reaction takes place at 10° C. also, it is much preferred that the reaction be carried out between 40° and 90° C. The polymer yields and the reaction rates will be higher. The catalyst too is present in low quantities. Furthermore, the superabsorbing properties of the products increase. Preferably, the aqueous polymerization mixture shall have a slightly acid pH. It is essential that the salification of the COOH functions take place after, not before the polymerization. In the latter case, the obtained copolymers would have mediocre properties. Advantageously soda or potash are used. It has been found that it is wholly possible to carry out the reaction in the presence of a nonallylated oligosaccharide. Therefore, in a variation of the invention the initial product is a mixture of allyldisaccharide with the following composition by weight:

| disaccharide | 10 to 20% |
| mono-allyldisaccharide | 25 to 35% |
| di-allyldisaccharide | 20 to 30% |
| tri-allyldisaccharide | 10 to 20% |
| tetra-allyldisaccharide | 5 to 7% |
| allyldisaccharide with a degree of substitution equal to or larger than 5 | <3.5% |

This mixture is well suited for the object of the invention, namely to achieve absorbent products. It was found, furthermore, that it is entirely possible to use the crude reaction mixture obtained by allylation of disaccharide as the initial product. Accordingly, a substantial saving is possible at this stage of the process. Preferably, the crude mixture has the following composition by weight:

30 to 50% of water
20 to 30% of an alkali metal halide
20 to 50% of allyldisaccharide Preferably, the allyldisaccharide will be allylsaccharose. Following the radical copolymerizing reaction of the mixture of allylsaccharose and acrylic derivative, the copolymer is precipitated while being agitated by methanol, filtered, washed with methanol, and oven-dried at a temperature of about 50° C. Furthermore, it is desirable to subject the dried copolymer to an additional purification stage by treating it, for instance, with water; the product gelled in this manner then is treated with methanol, filtered, and oven-dried. This teatment results in absorbing properties which exceed those of the initial copolymer. It is, furthermore, possible to lyophilize the purified copolymer in gelled form. This additional teatment results in products with exceptional bloodabsorbing properties hitherto never achieved to the knowledge of the applicant. The copolymers of the invention have particular application when used as superabsorbing additives in personal-hygiene products such as menstrual napkins, diapers for babies, or for incontinent adults. Moreover, these copolymers can be used in agriculture as moisture-retaining products particularly applicable to the hot regions of the globe They can also be used as humidity stabilizers in controlled hygrometric enclosures.

Another object of the invention as novel industrial products are the allyldisaccharides with a degree of substitution between 1.0 and 3.0. Preferably the allydisaccharide will be allylsaccharose. The allyldisaccharides can be prepared, for instance, by etherification of an alcohol function using an allyl halide. The reaction formula is given by:

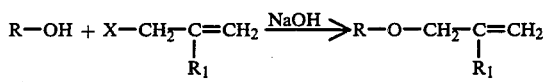

where
R = disaccharide radical
$R_1$ = H, $C_1$ to $C_4$ alkyl
X = Cl, Br

Preferably the non-substituted allyl derivative is used, that is, $R_1$ = H. For the allylation of saccharose, this process is illustrated in particular in U.S. Pat. No. 2,719,970 and in JACS 6746. However, these documents describe allylsaccharoses with high degrees of substitution, always in excess of 5, and unsuitable for the invention. Also, the invention activity of these products is justified by their making it possible to arrive at copolymers offering highly surprising absorbing properties.

The invention presently will be illustrated by the examples below:

ALLYLSACCHAROSE SYNTHESIS

EXAMPLE 1

278.1 g of saccharose with a molecular weight of 342, that is, 0.81 mole, and 66 g of NaOH in 75 ml of water are introduced in a one-liter reactor; within one hour 199.2 g of allyl bromide, i.e., 1.65 moles, are poured with agitation and maintaining the temperature at 85° C.; agitation and temperature are maintained for two hours until a pH of approximately 7 is obtained, then 200 ml of water are added. The compositon of the crude reaction mixture by weight is the following:

| unreacted sugar | 8.5% |
|---|---|
| allylsaccharoses | 35.0% |
| NaBr and by-products | 21.5% |
| water | 35.0% | and with the following molar distribution of the allylsaccharoses as measured by CLHP:

| unreacted sugar | 18.0% |
|---|---|
| allylsaccharose DS 1 | 30.9% |
| allylsaccharose DS 2 | 26.5% |
| allylsaccharose DS 3 | 15.1% |
| allylsaccharose DS 4 | 6.5% |
| allylsaccharose DS 5 | 2.2% |
| allylsaccharose DS 6 and beyond | 0.8% |

Accordingly, the mean degree of substitution of the mixture is 2.08 It is possible to eliminate the by-products of allyl alcohol and allyl derivative by entrainment by distillation of part of the water of the reaction mixture. However, this purification is unnecessary for the ultimate use of these products and the process thus is substantially simplified.

EXAMPLE 2

In order to minimize the formation of allylsaccharose with high DS, this test was carried out with a molar ratio of allyl bromide to saccharose of 1, that is, twice as weak as in the test of Example 1. The amounts used were as follows:

| saccharose | 278.1 g (0.81 moles) |
|---|---|
| allyl bromide | 96.6 g (0.8 moles) |
| NaOH | 50.0 g (1.25 moles) |
| | in 60 ml of water |

The allyl bromide was poured in over two hours at a temperature of 80° to 90° C., and after cooling the reaction mass was brought back to a pH of 7 by adding 160 ml of diluted hydrochloric acid. The total obtained mass is 620 g. The composition by weight of the reaction mixture is as follows:

| allylsaccharose + unreacted sugar | 48.5% |
|---|---|
| NaBr | 13.0% |
| NaCl | 4.0% |
| water | 34.5% | and the molar distribution of the allylsaccharoses is as follows:

| unreacted sugar | 40.6% |
|---|---|
| allylsaccharose DS 1 | 36.5% |
| allylsaccharose DS 2 | 16.5% |
| allylsaccharose DS 3 | 5.0% |
| allylsaccharose DS 4 | 1.1% |
| allylsaccharose DS 5 | 0.2% |
| allylsaccharose DS 6 | 0.03% |

This makes available a mixture which while containing more unreacted sugar also offers a higher proportion of DS 1 with respect to the allylsaccharoses of higher DS.

EXAMPLE 3

Allylsaccharose purification stage

Preparing the blend DS 1, 2, 3

The crude reaction mixture (820 g) obtained in Example 1 is placed in a liquid-liquid extractor and is continuously extracted using one liter of diethyl ether (chloroform also can be used). Following 24 hours of extraction, the etherified phase is separated from the aqueous phase and dried in the presence of sodium sulfate.

The ether evaporation makes it possible to obtain a fraction of allylsaccharose of 57 g and with a mean DS of 3.9 (set of the saccharoses with DS >3) which are distributed as follows:

| allylsaccharose DS 3 | 16 g |
|---|---|
| allylsaccharose DS 4 | 27 g |
| allylsaccharose DS 5 | 10 g |
| allylsaccharose DS 6 | <3 g |
| allylsaccharose DS 7 | <1 g |
| allylsaccharose DS 8 | <0.2 g |

The water in the aqueous phase is pressure and absolute ethanol is added so as to precipitate the sodium bromide which is a by-product of the condensation reaction. This sodium bromide is removed by filtration and this operation is repeated three times to eliminate most of the NaBr. In this manner a mixture with a mass of 278 g is recovered and consisting of unreacted sugar and of allylsaccharoses with DS<3 (means DS=1.40) and distributed as follows:

| | |
|---|---|
| unreacted sugar | 50 g |
| allylsaccharose DS 1 | 96 g |
| allylsaccharose DS 2 | 91 g |
| allylsaccharose DS 3 | 41 g |

Liquid chromatography of this mixture allowed isolating in pure form (95%) the DS 1 allylsaccharose.

EXAMPLE 4

Synthesizing the acrylic allylsaccharose copolymer

This test may be considered the most successful.

20 g of acrylic acid (0.277 moles) and 30 g of the crude mixture of the allylsaccharose of Example 1 (therefore containing about 10 g of allylsaccharose or 0.025 moles) and 80 g of additional water are placed in a one-liter flask at 80° C. and are agitated. Then the catalytic system consisting successively of 4 ml of aqueous solutions of 1% $FeSO_4$, 5% $NaHSO_3$, 10% $(NH_4)_2S_2O_8$ is then added. Very rapid exothermal gelling is observed. The copolymer obtained in elastic gel form is neutralized by a solution of methanolic potash in stoichiometric amounts, 18.3 g (0.278 moles) in 100 ml of methanol (85% KOH) with strong mechanical agitation. Then the salified copolymer cited above is treated with methanol in the mixer, filtered three times consecutively, oven-dried at a temperature of 40° to 50° C. 36.5 g of corresponding dry copolymer are obtained, corresponding to a yield by weight of 90% with respect to the active product used.

PURIFICATION 10 g of the above copolymer are gelled in 100 g of water, precipitated by methanol, filtered, and oven-dried at 40°–50° C. The purification yield is 84%. The product so purified offers higher performance.

EXAMPLE 5

This involves varying the amount of water during polymerization. Three tests 5a, 5b, 5c were carried out under the same conditions as in the test of Example 4 by changing the amount of additional water present in the medium, namely:

(As a reminder, Example 4 used 80 g of additional water.)
5a:0 g
5b:40 g
5c:160 g The yields are as follows:
5a:46%
5b:75%
5c:69%

The purification yields are as follows :
5b:81%
5c:77%

EXAMPLE 6

Varying the temperature.

Two tests were carried out under the same conditions as in the test of Example 4, varying only the copolymerization temperature, namely:
6a:39° C.
6b:50° C.

The yield is:
6a:18%
6b:43%

EXAMPLE 7

Proportions of salified COOH functions.

The process is the same as in that of Example 4 except that the degree of polymer salification is varied by changing the amount of the introduced mineral base. Soda was used in these tests, as follows:
7a:(0.278 mole×0.75)
7b:(0.278 mole×0.50)
7c:(0.278 mole×0.33)

Obviously the yields are identical provided the weight modification caused by a more or less complete salification is taken into account.

EXAMPLE 8

Synthesis with an allylsaccharose with a real DS=1 (per Example 3). 10 g of acrylic acid, that is 0.14 mole, are made to react with 5 g of pure allylsaccharose with a precise degree of substitution of 1 (obtained by preparatory chromatography), or 0.013 mole in 50% ethanol solution in the presence of 4 ml of catalytic solution as in the preceding examples and 40 g of water. Slower gelling is observed, and the gel is less "hard" then when using a total mixture of allylsaccharose. A temperature of 80° C. is maintained for one hour and 45 minutes. Neutralization is provided by 9.2 g of potash in 50 ml of methanol. The product is precipitated, washed, and dried at 40° C. The yield is 75%.

EXAMPLE 9

Synthesis using an allylsaccharose with a mean real DS>3.

The test is carried out under the same conditions as Example 8 and with an allylsaccharose with a mean degree of substitution of 3.9 and obtained by ether extraction from the crude mixture. The yield is 66%.

EXAMPLE 10

Acrylamide test.

50 g of acrylamide and 50 g of allylsaccharoses (crude reaction mixture from Example 1) are dissolved in 400 ml of water and heated while being agitated to 70°–80° C. The following then are sequentially added:
10 ml of 10% $H_2SO_4$
10 ml of isopropanol
10 ml of an aqueous solution of 10% ammonium persulfate The mixture gels, and 4 to 5 minutes after the addition of the ammonium persulfate solidifies as a whole. Thereupon a stoichiometric amount of soda is added in the form of the aqueous solution and the reaction mixture is made to reflux for 3 hours to hydrolyze the functions $-CONH_2$ into $-COONa$. Then the reaction mixture is treated following cooling in methanol and the separating copolymer is filtered off, then dried at room temperature under reduced pressure. The yield is 78%.

Absorbing properties of copolymers obtained in the tests described in the above Examples The retention of the water, which is saline in a concentration of 10 g/liter following immersion at 20° C. of an inert pouch consisting of 0.50 g of products over 36 $cm^2$ and then centrifugation at 1200 g for one minute, is measured. The product retention is determined by the difference of the retentions for a pouch, or napkin, with and without the product. Depending on the napkins having stayed three or 30 minutes in the saline water bath, the tests shall be respectively denoted by $R_3$ and $R_{30}$. These tests were mostly carried out on both purified and non-purified products. Also two tests were performed using two commercial products:

SANWET (polyacrylate starch), made by the Japanese firm of SANYO,
AQUA KEEP (polyacrylate), made by the Japanese firm of SEITETSU-PUK JAPAN.

The test results are listed in the table below:

TABLE

|  | Ex | $R_3$ | $R_{30}$ | $R_{30}$ after purification |
|---|---|---|---|---|
| Reference | 4 | 25 | 35 | 45 |
| Varying Amount | 5a | 11.5 | 20 | — |
| Of Water | 5b | 18 | 20 | 23 |
|  | 5c | 13.5 | 20 | 32 |
| Varying Temperature | 6a | 7.5 | 10 | — |
|  | 6b | 23 | 27 | — |
| Varying Salt | 7a | 16 | 25 |  |
| Concentration | 7b | 26 | 31 |  |
|  | 7c | 13 | 23 |  |
| DS = 1 | 8 | 2.5 | 2.5 | — |
| DS = 3.9 | 9 | 9 | 9 | — |
| Acrylamide allylsaccharose | 10 | — | 17.5 | 37.5 |
| SANWET ® |  |  | 32 |  |
| AQUA KEEP ® |  |  | 33 |  |

Application of the copolymers described in the above tests as improved retention additives in absorbing pads 1 g of the copolymer obtained in Example 4 is spread over a surface of 36 cm² of a menstrual mapkin with an area of 36 cm². Then the napkin is immersed into a mixture simulating the menstrual blood at 20° C. and of the following weight composition:

| beef blood | 8.5% |
| saline water, 9 g of NaCl/liter | 15% |
| heparinate | 25 mg/l | either for 3 minutes ($R_3$) or for 30 minutes ($RS_{30}$). The material is weighed after centrifugation and the data is related to the results obtained for a menstrual napkin without copolymers. A test also was run when the same copolymer has lyophilized. The following results were obtained:

| $R_3$ | 4.5 |
| $R_{30}$ | 10.5 |
| $R_{30}$ lyophilized product | 20 |
| $R_{30}$ SANWET ® | 13 |
| $R_{30}$ AQUA KEEP ® | 11 |
| $R_{30}$ lyophilized SANWET ® | 12 |
| $R_{30}$ lyophilized AQUA KEEP ® | 12 |

I claim:

1. A salified acrylic allyloligosaccharide copolymer characterized in that it consists in a chemically combined form of at least one allyloligosaccharide with a mean degree of substitution less than 4 per oligosaccharide molecule and of at least one acrylic derivative with partly or totally salified carboxyl functions, said copolymer, following 30 minutes in water with a salt content of 10 g/liter, evincing a degree of retention in excess of 8 g of saline water per gram of copolymer.

2. Salified acrylic allyloligosaccharide copolymer of claim 1, characterized in that the mean degree of substitution per molecule of oligosaccharide is less than 3 and larger than or equal to 1.

3. Salified acrylic allyloligosaccharide copolymer of claims 1 or 2, characterized in that the allyloligosaccharide is an allyldisaccharide.

4. Salified acrylic allyloligosaccharide copolymer of claim 3, characterized in that the allyldisaccharide is allylsaccharose.

5. Salified acrylic allyloligosaccharide copolymer of claim 1, characterized in that the acrylic derivative is selected from the methacrylic or acrylic acid, the amide of the acrylic or methacrylic acid, whether alone or in mixtures.

6. Salified acrylic allyloligosaccharide copolymer of claim 1, characterized in that the allyloligosaccharide with a mean degree of substitution less than 4 consists of an allyloligosaccharide of a mean degree of substitution less than 3 and of an allyloligosaccharide of a mean degree of subsitution exceeding 5.

7. Salified acrylic allyloligosaccharide copolymer of claim 1, characterized in that at least 10% of the carboxyl groups are salified.

8. Salified acrylic allyloligosaccharide copolymer of claim 1, characterized in that the allylic/acrylic molar ratio is between 0.005 and 1.

9. Salified acrylic allkyloligosaccharide copolymer of claim 3, characterized in that the composition by weight of the copolymer is

| allyldisaccharide | 5 to 30% |
| monoacrylic derivative | 70 to 95%. |

10. Salified acrylic allyloligosaccharide copolymer of claim 9, characterized by the composition by weight of the copolymer being

| allyldisaccharide | 8 to 25% |
| monoacrylic derivative | 75 to 92%. |

11. A process for preparing a salified acrylic allyloligosaccharide copolymer characterized in that an acrylic derivative is reacted with a mixture of allyloligosaccharides with a mean degree of substitution less than 4 per oligosaccharide molecule at a temperature in excess of 10° C. in the presence of a radical polymerization initiator and in that the obtained copolymer is partly or totally salified by a strong mineral base and then is dried.

12. Preparation process, for a salified acrylic allyloligosaccharide copolymer of claim 11, characterized in that the mixture of allyloligosaccharides is aqueous.

13. Preparation process for a salified acrylic allyloligosaccharide copolymer of claim 12, characterized in that the aqueous allyloligosaccharide mixture includes at least 5 g of water per 10 g of allyloligosaccharide.

14. Preparation process for a salified acrylic allyloligosaccharide copolymer of claim 11, characterized in that the copolymerization reaction takes place at a temperature equal to or larger than -40° C. and less than 90° C.

15. Preparation process for a salified acrylic allyloligosaccharide copolymer of claim 11, characterized in that the allyloligosaccharide mixuture is a mixture of allyldisaccharides with the following weight composition:

| | |
|---|---|
| saccharose | 10 to 20% |
| mono-allyldisaccharide | 25 to 35% |
| di-allyldisaccharide | 20 to 30% |
| tri-allyldisaccharide | 10 to 20% |
| tetra-allyldisaccharide | 5 to 7% |
| allyldisaccharide with a degree of substitution equal to or larger than 5 | <3.5% |

16. Preparation process for a salified acrylic allyloligosaccharide copolymer of claim 15, characterized in that the aqueous mixture of allyldisaccharide consists by weight of:
   30 50% of water
   20 to 30% of an alkali metal halide
   20 to 50% of allyldisaccharide.

17. Preparation process for a salified acrylic allyloligosaccharide copolymer of claim 12, characterized in that the aqueous mixture has a pH slightly less than 7.

18. Preparation process for a salified acrylic allyloligosaccharide copolymer of claim 11, characterized in that drying is implemented by methanol washing followed by oven-drying.

19. Preparation process for a salified acrylic allyloligosaccharide copolymer of claim 11, characterized in that the copolymer is next gelled, precipitated and purified with methanol or ethanol.

20. Preparation process for a salified acrylic allyloligosaccharide copolymer of claim 11, characterized in that the copolymer is lyophilized.

21. Application of the salified acrylic allkyloligosaccharide copolymers of claim 1, characterized by being used as an additive in the absorbing pads of sanitary napkins, baby diapers, or incontinent-adult diapers.

* * * * *